United States Patent
Heinz et al.

(10) Patent No.: US 7,371,222 B2
(45) Date of Patent: May 13, 2008

(54) CERVICAL SUPPORT SYSTEM

(75) Inventors: Thomas J. Heinz, La Canada, CA (US); Royce Rumsey, Laguna Beach, CA (US)

(73) Assignee: Biocybernetics International, Laverne, CA (US)

( * ) Notice: Subject to any disclaimer, the term of this patent is extended or adjusted under 35 U.S.C. 154(b) by 145 days.

(21) Appl. No.: 10/966,099

(22) Filed: Oct. 18, 2004

(65) Prior Publication Data
US 2005/0113728 A1 May 26, 2005

Related U.S. Application Data

(60) Provisional application No. 60/549,140, filed on Mar. 3, 2004, provisional application No. 60/511,701, filed on Oct. 17, 2003.

(51) Int. Cl.
*A61F 5/00* (2006.01)
(52) U.S. Cl. .................... 602/18; 602/20; 128/DIG. 23
(58) Field of Classification Search .................. 602/18, 602/20, 17, 32–36; 128/845, 846, 869, 870, 128/DIG. 23
See application file for complete search history.

(56) References Cited

U.S. PATENT DOCUMENTS

| | | | | | |
|---|---|---|---|---|---|
| 2,102,069 | A | * | 12/1937 | Hanicke | 602/18 |
| 2,692,595 | A | * | 10/1954 | Blair, Jr. | 602/17 |
| 3,177,869 | A | * | 4/1965 | Bartels | 602/18 |
| 3,220,406 | A | * | 11/1965 | Connelly | 602/18 |
| 3,313,297 | A | * | 4/1967 | Applegate et al. | 602/18 |
| 3,345,983 | A | * | 10/1967 | Denney, Jr. | 602/18 |
| 3,507,273 | A | * | 4/1970 | Yellin | 602/18 |
| 3,601,123 | A | * | 8/1971 | McFarland | 602/18 |
| 3,834,048 | A | * | 9/1974 | Maurer | 36/50.1 |
| 4,862,878 | A | * | 9/1989 | Davison et al. | 602/20 |
| 5,005,563 | A | * | 4/1991 | Veale | 602/18 |
| 5,201,702 | A | * | 4/1993 | Mars | 602/17 |
| 5,411,471 | A | * | 5/1995 | Terrazas | 602/18 |
| 5,531,669 | A | * | 7/1996 | Varnau | 602/18 |
| 5,688,229 | A | * | 11/1997 | Bauer | 602/18 |
| 6,071,255 | A | * | 6/2000 | Calabrese | 602/18 |
| 6,254,560 | B1 | * | 7/2001 | Tweardy et al. | 602/18 |
| 6,447,468 | B1 | * | 9/2002 | Hankins et al. | 602/18 |
| 6,494,854 | B1 | * | 12/2002 | Visness et al. | 602/18 |
| 2004/0204666 | A1 | * | 10/2004 | Marsh | 602/18 |

* cited by examiner

*Primary Examiner*—Justine R. Yu
*Assistant Examiner*—Shumaya Ali
(74) *Attorney, Agent, or Firm*—MacPherson Kwok Chen & Heid LLP; Mark Pellegrin

(57) ABSTRACT

A cervical support system for restricting head and neck movement of a patient recovering from an injury to or surgery on the spine. The support system includes a supporting member for mounting onto and around the head and neck of the patient. The supporting member includes an injection molded base portion integral with an occipital lobe supporting portion. The base portion is arranged to rest on the shoulder of the patient while the occipital lobe supporting portion is arranged to extend along the neck from the shoulder to the head of the patient. An arcuate member such as a C-collar is disposed on an outer surface of the supporting member. A plurality of adjustment devices such as a turn-tab adjustment mechanism on an outer surface of the arcuate member rotatably connect the arcuate member to the supporting member to position the arcuate member onto, and with respect to, the supporting member.

17 Claims, 6 Drawing Sheets

CERVICAL SUPPORT SYSTEM

This application claims priority to applicants' U.S. Provisional Application Ser. No. 60/511,701 entitled "CRESCENT SHAPED CERVICAL COLLAR" filed Oct. 17, 2003, and U.S. Provisional Application Ser. No. 60/549,140 entitled "CRESCENT SHAPED CERVICAL COLLAR II" filed Mar. 3, 2004. The entirety of these patent applications is incorporated herein by reference.

BACKGROUND OF INVENTION

1. Field of the Invention

The present invention relates to a cervical support system and complementary features of the cervical support system. More specifically, the present invention relates to a cervical support system that can have a crescent shape so that it is quick and easy to install on a patient, and provides a comfortable fit, so that the patient can wear the support system in compliance with the physician's orders.

2. Description of the Related Art

A cervical collar is a medical device for temporarily restricting movement of the head and neck. The cervical collar is placed on a patient after an injury to or surgery on a cervical portion of the spine. The success of patient recovery from an injury to or surgery on the cervical portion of the spine depends on a number of factors including patient compliance with wearing the collar. However, the most reported concern raised by physicians of patients with spinal column injuries is lack of patient compliance with the physician's orders to wear the collar for the required recuperative duration. Existing cervical collars, in general, form a 360-degree enclosure of the neck. As a result, existing cervical collars retain body heat due to the 360-degree enclosure and give patients the feeling of being choked, causing overall patient discomfort. Further, existing cervical collars unnecessarily restrict movement of the mandible, thus, limiting or preventing the patient from being able to talk and/or eat. Thus, patients complain of skin irritation or chafing as a result of a natural attempt to talk and/or eat while wearing the 360-degree enclosure.

While existing cervical collars provide some restrictive range of motion of the head and neck, they significantly compromise or fail to deliver sufficient support and/or immobilization requisite for patient recovery and/or re-injury.

The cervical support system of present invention addresses patient complaints, such as insufficient recuperative support and immobilization, and also reduces patient discomfort in at least the above-noted areas of concern. For example, the system of the present invention at least reduces patient heat discomfort and the choking feeling inherent in the existing cervical collars. The system is an orthotic for the cervical spine that increases patient compliance by eliminating problems inherent in existing cervical collars. The effect of the cervical support system of the present invention is patient compliance through improved support and comfort. As a result, the patient can wear the cervical support system for the required recuperative duration with increased comfort, control and support, thereby promoting faster healing of the injury.

SUMMARY OF THE INVENTION

The present invention relates to an improved cervical support system including a collar for restricting head and neck movement to promote healing after an injury to the spinal column. The present invention includes a cervical support system with integrated adjustments for customizing the system for different sized patients and applying the collars quickly and easily. The support system of the present invention provides full exposure of the cervical portion of the spine at a front portion of the support system. The support system of the present invention provides the support to the head and neck, and restricts lateral, sagittal and coronal movement, while significantly improving comfort, reduction of heat buildup through complete integrated ventilation.

Among other benefits, the present invention allows the patient to talk and eat while wearing the system. In addition, the geometry of support system of the present invention allows a physician to check the injury or typical incision from surgery without removing the support system. The present invention provides the aforementioned benefits with a crescent shape that allows full exposure of the cervical portion of the spine at the front of the support system. Accordingly, the support system of the present invention significantly improves the fit and comfort to the patient.

The present invention allows ease of use for the physician, but also, generates significant improvements in patient comfort and therefore a complementary improvement in patient compliance with the physician's order for treatment. For the patient, the open front design of the support system of the present invention allows for improved air circulation and therefore, significantly reduces accumulation of the patient's body heat within the support system. As a result, the patient can wear the support system more comfortably and for a longer duration of time. The open front design of the support system of the present invention allows the patient to talk comfortably with less restriction around the chin and jaw while simultaneously providing improved critical head, neck and shoulder support, and without losing critical head and neck support. Unlike the cylindrical shape of the existing cervical collars that transfer the load of the head and the neck to the sternum and collarbone, the support system of the present invention transfers the load of the head and neck throughout the trapezius area to the stronger pectoral muscles and shoulder blades. This transfer and dispersion of weight over stronger, less sensitive, areas of the body provides another aspect of comfort and control for the patient, leading to increased compliance. Further, the placement of foam liners on primary contact surfaces of the support system with the patient's body also improves patient comfort. The support system of the present invention also includes an occipital/deltoid support member that provides a significant increase in occipital bone support and weight distribution, and additional support in the trapezius area of the patient.

For the physician, the support system of the present invention allows easier application and removal, as compared to existing cervical collars. Mandible supports of the support system help the physician precisely adjust the support system to the patient, and provide greater patient comfort. The mandible supports can include adjustable contoured chin cradles that provide a custom-fit cradle underneath the mandible area of the body for a more secure support. As a result, physicians will find positioning the patient's head and neck in the support system to be significantly easier. Furthermore, the support system has an open front so that the physician can easily examine surgical incisions, and the healing of the same without having to remove the support system. In addition, the ability to customize a single support system of the present invention to a wide variety of body sizes and types enables the physician to reduce the number of different sized support systems that must be stocked to accommodate different sized patients. The present invention also allows easy and secure setting of the orthotic to the size of the patient and thereby eliminates the need to frequently adjust and readjust the orthotic.

In accordance with the first embodiment of the present invention, the cervical support system includes a crescent shaped collar The system also includes a mandible securement device to assist the physical or orthotist in determining the optimum position of a cantilevered lower head support, a major feature of the support system of the present invention. The crescent shaped collar of the first embodiment of the present invention can be designed with a vertically oriented hinge and spring combination at the rear center of the collar. The hinge and spring combination dissects the collar equidistantly from the centerline of the neck at the rear of the brace. Opening or widening the collar releases the torsion spring so that the collar can be placed on the patient and retractably closed around the patient's neck. The hinge and spring combination can include mechanical members with an adjustable spacer in the hinge area to open the collar for use. The collar can also be designed as a polymeric molded member having a rear portion with a geometry that allows the collar to be pulled apart from the front like a clamshell, and then placed around the neck of the patient from the rear. As such, the inherent elastic characteristic of a polymeric collar acts as a mechanical hinge and spring combination. All adjustments can be completed prior to placing the support system on the patient. Thus, once the support system is properly adjusted for the patient, applying and/or removing the support system takes less than three seconds.

In a second embodiment of the present invention, the physician or orthotist provides general size/placement (on a 9-point adjustable matrix) of the mandible support before the support system is placed on the patient. A 270-degree or more rotationally adjustable cradle conforms to the patient's chin contour/position for maximum comfort. Then the mandible support is secured into place. The mandible support and chin cradle determines the optimal position of the cantilevered lower head support.

The turn-tab adjustments on the 9-point adjustable matrix and the rotational chin cradle can be adjusted, by loosening or tightening, to secure the mandible support in an optimal size, position, and contour. The support system of the second embodiment of the present invention is designed with a vertically oriented occipital/deltoid support member and horizontally oriented side components. The occipital/deltoid support member provides torsion-compression of the side components, which are held together at the center rear portion of the collar, and thereby adjustable sizing and contouring of the collar. The collar can be pulled apart from the front like a clamshell, and then simply placed around the neck from the rear. Releasing the collar releases the torsion spring and closes around the neck. No further adjustments are required because the adjustments can be completed before placing the support system on the patient. Once the support system of the second embodiment of the present invention is properly adjusted to the patient, applying and/or removing takes less than five seconds.

Additional advantages and novel features of the invention are set forth in the attachments to this summary, and in part will become more apparent to those skilled in the art upon examination of the following or upon learning by practice of the invention.

BRIEF DESCRIPTION OF THE DRAWINGS

The features of the invention will be more readily understood with reference to the following description and the attached drawings, wherein.

DETAILED DESCRIPTION OF THE INVENTION

The present invention is directed to a cervical support system for restricting movement of the head and neck of a patient to facilitate recovery from an injury to or surgery on the cervical portion of the spine. The present invention includes a number of components and adjustment devices so that the support system can be custom-sized by a physician or orthotist to meet the particular physical proportions of the patient. In addition, the support system of the present invention includes features that make it easier for the patient to wear, as required by the physician. As a result, patient compliance with the physician's order to wear a cervical support system can be significantly improved.

Figure 1:
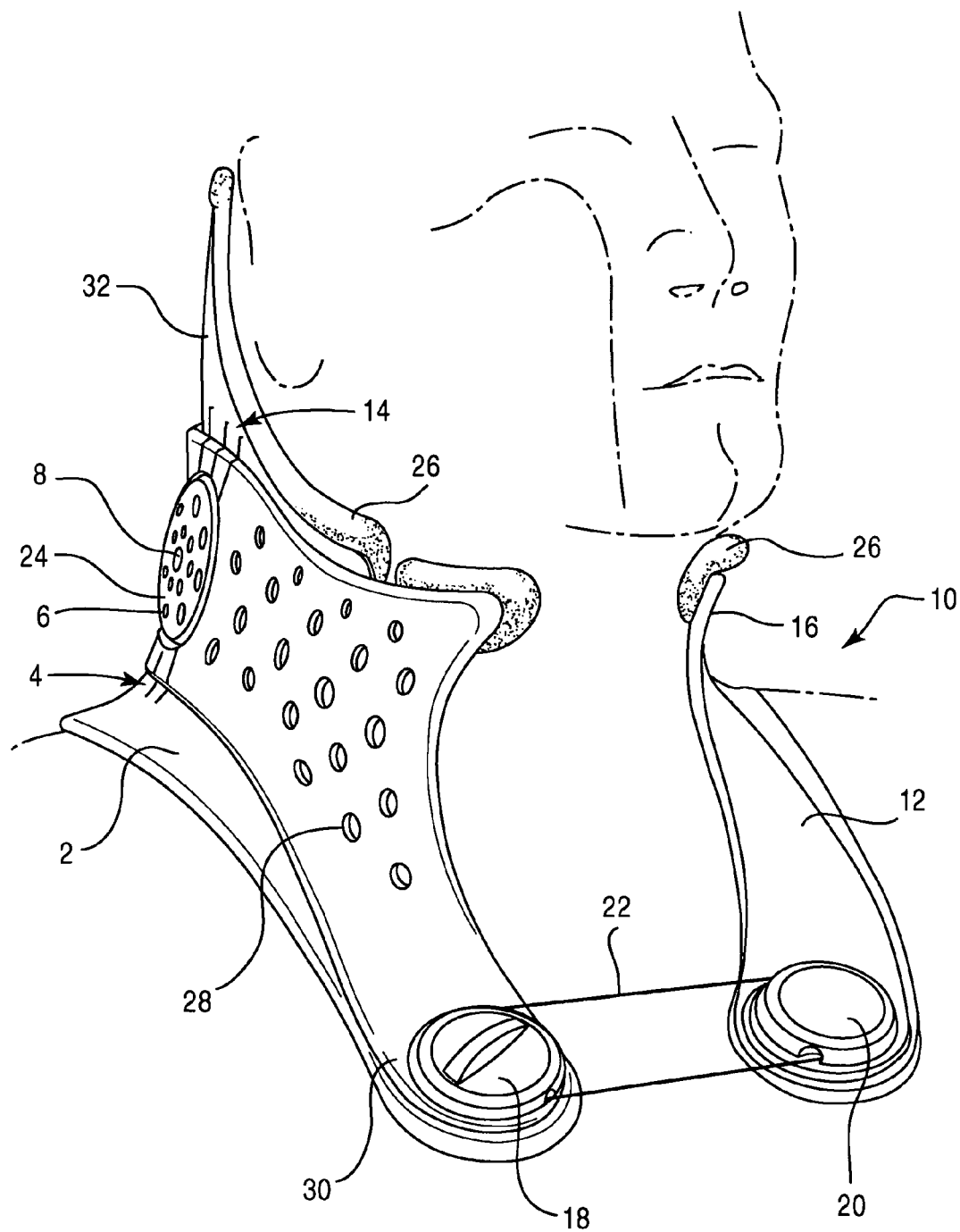
FIG. 1 illustrates a front perspective view of the cervical support system according to a first embodiment of the present invention.

In the first embodiment of the present invention, shown in FIG. 1, the cervical support system 10 is illustrated as having a C-shape, wishbone shape, or crescent shaped design when viewed from the front as worn by the patient. The support system 10 is designed to partially encircle the patient's neck, leaving the front of the support system open to provide full exposure of the cervical portion of the spine. The support system 10 includes an inner shell and an outer shell. The inner shell can be formed as an injection molded curved base portion 2 integrally formed with an occipital lobe and rear mandible support 32. The outer shell can be formed as a thermo-molded C-collar 12. The combination of the inner shell and outer shell restrict lateral, sagittal and coronal movement of the neck and head.

The outer shell or C-collar 12 is mounted onto the external surface of the inner shell, parallel to the occipital lobe and rear mandible support 32 and perpendicular to the base 2. A side view of the support system 10 would show that an upper surface of the base portion 2 and corresponding adjacent edge of the C-collar 12 have a supine or sine wave shaped profile that allows the base 2 of the support system 10 to conform to the curvature of the patient's shoulders. The front perspective view shown in FIG. 1 illustrates that the inner and outer shells, namely the base 2, occipital lobe and rear mandible support 32, and C-collar 12, respectively, conform to the curvature of the patient's head and neck.

The C-collar 12 includes a plurality of ventilation and weight reduction holes 28 therethrough, which serve to reduce heat buildup between the patient's body and the support system, and also reduce the overall weight of the support system. The ventilation and weight reduction holes 28 improve air circulation between the patient's body and the support system as air circulates through the open space in front, and continues through the ventilation and weight reduction holes 28, encircling the sides and rear of the support system. As such, the patient can be more comfortable wearing the support system.

The C-collar 12 can be formed from a polymeric material such as, for example, polycarbonate or Acrylonitrile Butadiene Styrene (ABS). The base portion 2 and integrally molded occipital lobe and rear mandible support 32 can be injection molded from any suitable polymeric material including, but not limited to polyethylene.

In use, the occipital lobe and rear mandible support 32 of the inner shell is disposed against the neck of the patient and the base portion 2 rests on the shoulder of the patient. In this arrangement, the load of the head and neck is transferred to the pectoral muscles and shoulder blades, which are stronger areas in the head and neck region of the body. The occipital lobe and rear mandible support 32 supports the back of the head in the area of the occipital lobe.

In addition to providing the physician with an easy access of the cervical portion of the spine, the open front of the support system also reduces heat buildup inside of the support system. Further, the open front of the support system allows the patient to be able to talk while wearing the support system without losing critical head and neck support.

The outer shell or C-collar 12 also includes integrally formed cantilevered lower head supports 16. The lower head supports 16 are curved in an outwardly direction hold the head and neck in place and allow the patient to be able to talk to freely with minimal physical restraint.

The base 2, occipital lobe and rear mandible support 32, and C-collar 12 include a plurality of rotation and size placement indexes 4, 14 for vertically, horizontally, and angularly setting the position of C-collar on the occipital lobe and rear mandible support 32 and the base 2. The rotation and size/placement indexes 4, 14 help guide the physician to place the C-collar in the optimum vertical, horizontal and angular position on the inner shell forming the integrated base and occipital lobe and rear mandible support.

A mandible securement device 24 is provided on an outer surface of the C-collar 12 on both sides. The mandible securement device 24 can rotate 90-degrees in a clockwise or counterclockwise direction in order to adjust the angular position of the C-collar 12. The mandible securement device 24 can also move the C-collar 12 on the inner shell vertically and horizontally as indicated by the rotation and size/placement indexes 4 and 14, respectively. Mandible securement device 24 includes a plurality of dimples 6 on an external surface for engagement with a specially keyed tool (not shown) so that the mandible securement device 24 can be rotated. The use of the specially keyed tool prevents the patient from self-adjusting the mandible securement device 24. The mandible securement device 24 also includes rotational adjustment insert 8, which extends through the C-collar 12 to the occipital lobe and rear mandible support 32 to fix the C-collar in position.

Additional patient comfort according to the first embodiment of the present invention includes a plurality of removable padding that can be disposed on the inner surface of the shell and arranged at points where the shell contacts the patient's skin. See FIG. 1. For example, foam liners 26 are comfortable lightweight padding that can be applied between the patient's skin and the support system. The liners can be cut to form and disposed on an inner surface of the occipital lobe and rear mandible support 32, and on an inner surface of the C-collar 12 of the shell. Foam liners can also be disposed on the cantilevered lower head supports 16 to contact the patient's body at the jaw line. For example, as shown in FIG. 1, foam liners 26 are disposed at an upper front edge of the C-collar 12 of the shell. The liners 26 can be formed from any material that can provide a comfortable padding between the patient's skin and the support system. The padding of the present invention can be removable, washable and reusable.

In order to secure the lower portion of the support system in position on the patient's body, the C-collar 12 has a pair of the elongated ends 30 on which are mounted a thumb wheel tension/fit adjustment device. The device includes a thumb wheel 18, a pivot 20 and tensile member such as a cable or parachute cord 22 for securing the elongated ends of the C-collar 12 in place on the patient. The thumb wheel 18 and pivot 20 can be provided on either one of the elongated ends 30 of the shell. The cable 22 extends between the thumb wheel 18 and pivot 20 in the manner of a pulley such that rotation of the thumb wheel 18 creates tension in the cable 22. The thumb wheel can be rotated 360-degrees in a clockwise or counterclockwise direction. Rotation of the thumbwheel in a direction opposite from the tightening direction releases the tension in the cable 22. The thumbwheel 18 and pivot 20 can be formed from any suitable polymeric material, while the cable 22 can be formed from a material such as a low friction cord.

The second embodiment of the present invention will now be described with reference to FIGS. 2 and 3. As shown in the front perspective of FIG. 2, the cervical support system 110 includes a pair of side components 112 each having a mandible support arm 114 mounted thereon, and an occipital/deltoid support member 132. A side view of the support system 110 shows that the side components 112 have a supine or sine wave shaped design that allows the support system to conform to the curvature of the head, neck and shoulders of the patient's body. The cervical support system 110 can be made from nylon, stainless steel, or a polymeric material such as Acrylonitrile Butadiene Styrene (ABS), polycarbonate, polyurethane, or acetal.

Figure 2:
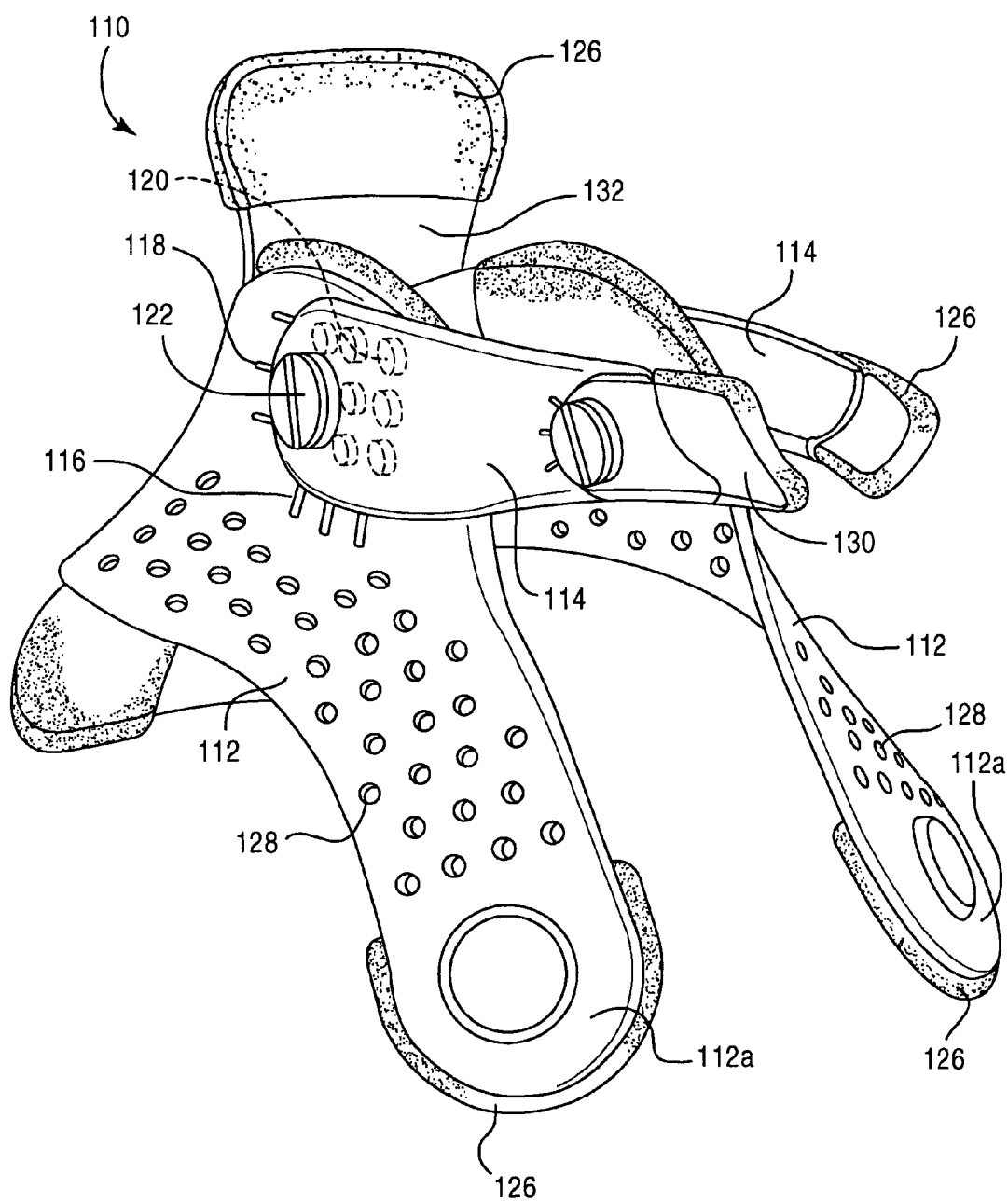
FIG. 2 illustrates a front perspective view of the cervical support system according to a second embodiment of the present invention.

As shown in FIG. 2, for example, the side components 112 are provided with a plurality of ventilation and weight reduction holes 128. Air circulates through the open space between the side components 112, and continues through the ventilation and weight reduction holes 128 in the surfaces of support system 110 of the present invention, encircling the sides and rear of the support system. The ventilation and weight reduction holes 128 are formed by removing material from the system, thereby reducing the overall weight of the collar 110 leading to greater patient comfort and compliance.

Figure 3:
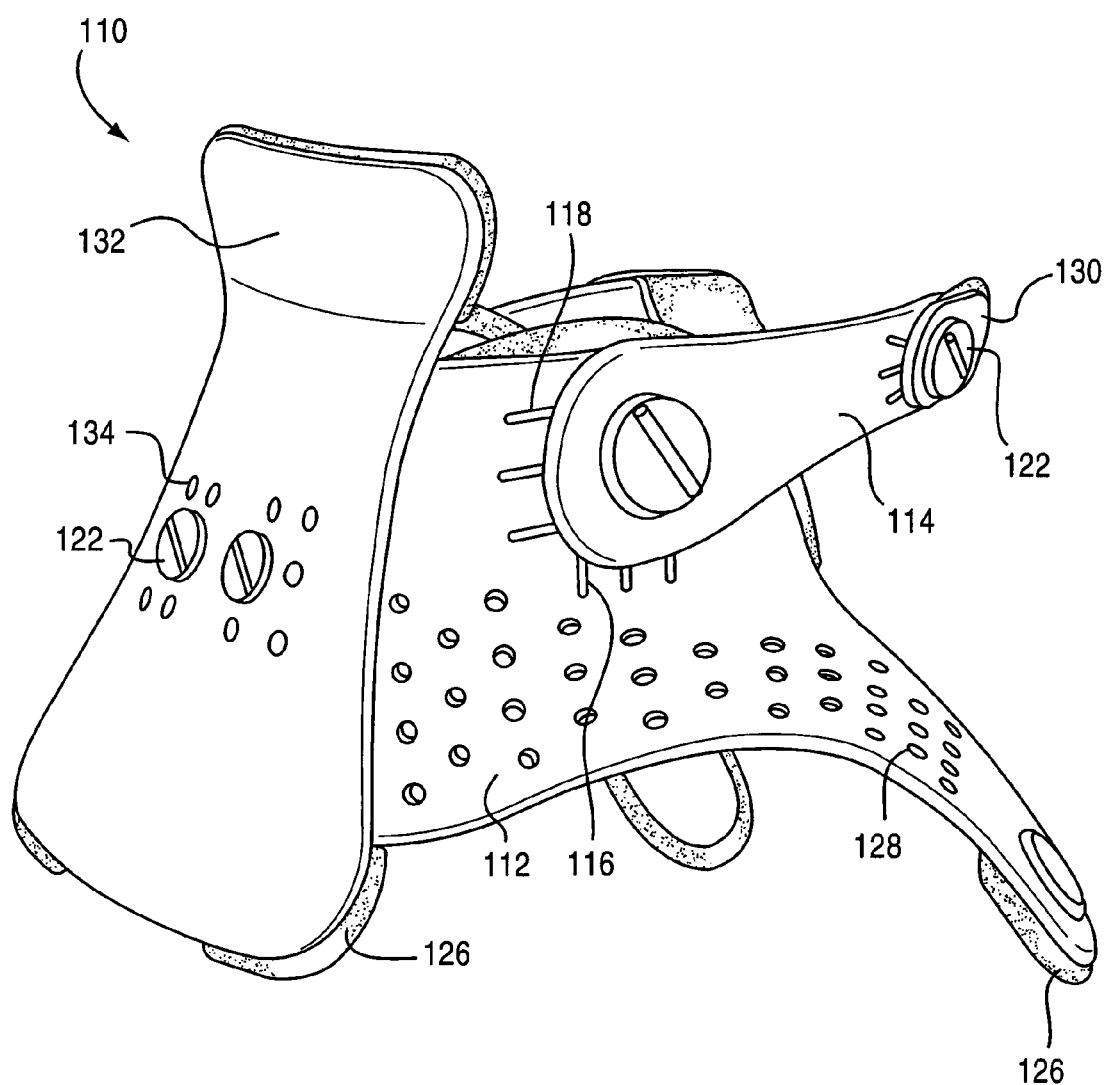
FIG. 3 illustrates a rear perspective view of the cervical support system according to the second embodiment of the present invention.

As shown in FIGS. 2 and 3, the mandible support arms 114 are elongated members adjustably mounted by their proximal ends onto an upper portion of the side components 112. The distal ends of the mandible supports are illustrated as extending in a forward direction toward the open front of the support system 110. The adjustable mounting of the mandible support arm 114 allows the supports to be vertically, horizontally and angularly positionable on the side components 112. Vertical size/placement indexes 116, and horizontal/size placement indexes 118 in the form of markers on the external surface of the side components 112, help guide the physician in adjusting the mandible support arms 114 to the most suitable customized arrangement. FIGS. 2 and 3 illustrate, for example, three size/placement indexes in each of the vertical and horizontal directions, indicating at least nine adjustment positions. As such, the mandible supports can have about 270-degrees of adjustment. Additional vertical and horizontal size/comforts adjustments can be used to provide additional adjustment positions.

The mandible support arms 114 include at least one threaded boss 120. A turn-tab adjustment mechanism 122, as will be discussed below, is inserted into and passed through the threaded boss 120 of the mandible support arm 114 to one of a plurality of threaded bosses 120 in the side components 112 to secure the mandible support arm 114 in the desired position on the side component 112. In view of the identifying size/placement indexes 116, 118, the turn-tab adjustment mechanism 122 can thus secure the mandible support arms 114 to the side components 112 in at least nine different positions.

Rotational axis or cantilevered front and lower head supports 130 are shown in FIGS. 2 and 3 as adjustably mounted onto the distal end of the mandible support arms 114 toward the front of the support system. The cantilevered lower head supports 130 hold the head and neck in place and allow the patient to be able to talk to freely with minimal physical restraint. The lower head supports 130 can rotate 180-degrees to be adjustable for increased patient support and comfort. The rotational axis or cantilevered front and lower head supports 130 are also attachable to and adjustable on the mandible support arms 114 by a turn-tab adjustment mechanism 122. An inner surface of the lower head supports 130 can be provided with removable padding 126 such as foam liners or insert molding that can be placed on an interior surface of the lower head supports 130 at primary contact points with the patient's body. The padding can be made from polyurethane, for example, and shaped to fit the patient's jaw line. Further, the padding can be removable, washable and reusable.

FIG. 3 illustrates a rear perspective view of the support system 110 showing the occipital/deltoid support member 132, which is located at a rear portion of the support system 110 and bridges the side components 112. The occipital/deltoid support member 132 provides a significant increase in occipital bone support and weight distribution and additional support to the trapezius area. The coupling of the occipital/deltoid support member 132 with the side components 112 creates a simultaneous torsion-compression of the side components, which are held together and the center rear portion of the support system 110.

As shown in FIG. 3, the occipital/deltoid support member 132 includes multiple circumferential and height adjustment apertures 134 for adjusting the circumferential size of the support system and the optimum height of the occipital/deltoid support member 132. The occipital/deltoid support member 132 and the rear portion of each side component 112 include threaded bosses for attaching turn-tabs adjustment mechanisms 122 thereto and securely mount the occipital/deltoid support member 132 to the side components. The turn-tab adjustment mechanism 122 as described below, fixes the occipital/deltoid support members in position with the side components. With the circumferential and height adjustment apertures 134 and turn-tab adjustment mechanisms 122, the occipital/deltoid support member 132 and the side components 112 can be adjusted using different apertures 134, allowing the support system to accommodate a patient's weight gain or weight loss.

The interior surface of the occipital/deltoid support member 132 can include a lightweight padding 126 such as foam or insert molding on primary contact points with the patient's body for greater patient comfort and compliance. The padding can be removable, washable and reusable.

The side component 112 have elongated ends 112a which can be stabilized on the patient's body by harnessing the ends 112a to each other with a Velcro® strap (not shown) that spans the front opening of the support system 110. The strap thus extends between the lowermost points of the support system.

Figure 4B:
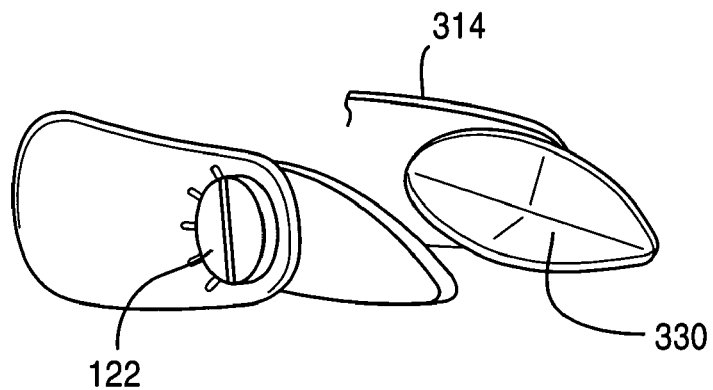
FIGS. 4a and 4b illustrate a front perspective view of the cervical support system according to a third and fourth embodiment, respectively, of the present invention.
Figure 4A:
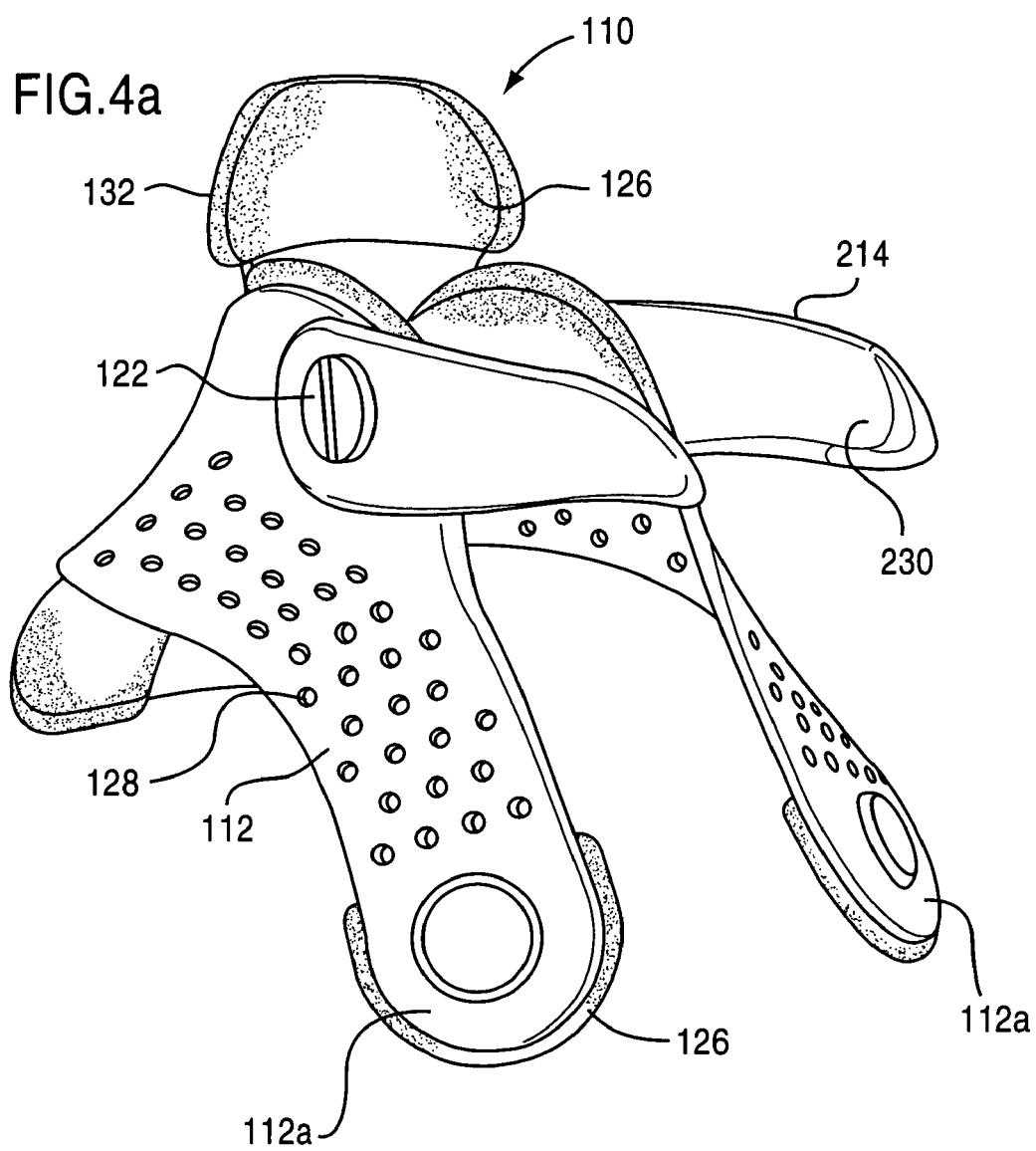

The third and fourth embodiments of the invention will now be described with reference to FIGS. 4a and 4b. Reference numerals for the same elements in FIGS. 2 and 3 refer to the same elements in FIGS. 4a and 4b. In the third embodiment of the present invention, illustrated in FIG. 4a, the mandible support 214 can include a chin cradle 230 on an interior surface thereof. In a fourth embodiment of the present invention, illustrated in FIG. 4b, the mandible support 314 can include a pivotable chin cradle 330. The chin cradles 230, 330 are fitted underneath the mandible area of the patient's jaw to provide a more secure support and positioning of the patient's head in the support system. The chin cradles 230, 330 can have a concave shape that fits with the patient's jaw line and help the physician determine the precise angle and location for the mandible supports to provide improved comfort to the patient so that the support system comfortably follows the contour of the patient's body.

Figure 5:
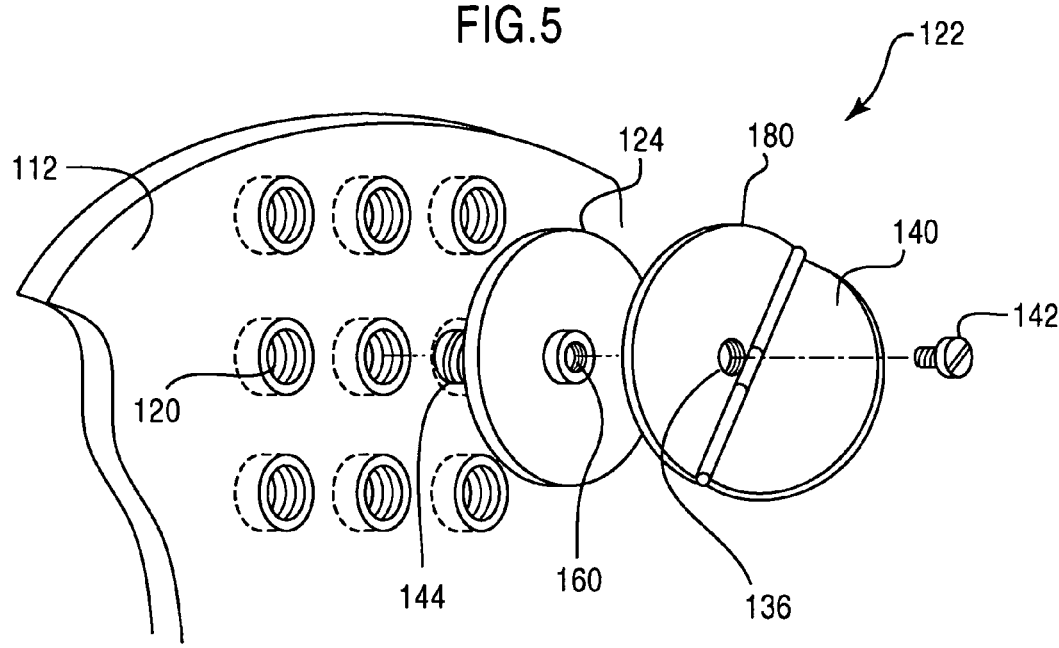
FIGS. 5, illustrates an exemplary attachment device according to the present invention.
Figure 6:
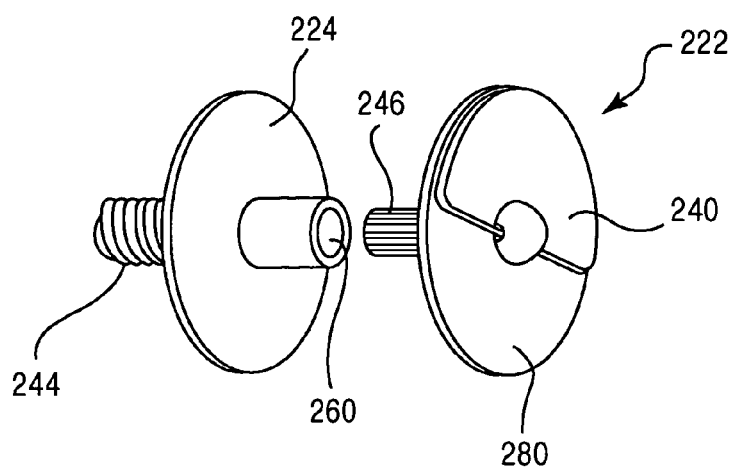
FIG. 6 illustrates an exemplary attachment device according to the present invention.

FIG. 5 illustrates an example of the turn-tab adjustment mechanism 122 of the present invention as it is threaded into the bosses 120 located in the mandible support arm 114, occipital/deltoid support 132 and/or rear portions of the side components 112. FIG. 6 illustrates an enlarged view of the turn-tab adjustment mechanism 122.

The turn-tab adjustment mechanism 122 is a self-contained turn-tab, which secures one component to another component. The turn-tab adjustment mechanism 122 allows a first component to be easily attached to, or detached from, a second component, through clockwise and counterclockwise rotation of the turn-tab adjustment mechanism 122. For example, as discussed above, the turn-tab adjustment mechanism can be used to secure and release the mandible support arm 114 to and from the side component 112. In the present invention, the turn-tab adjustment mechanism 122 also allows for easy attachment and detachment of side components 112, and occipital/deltoid support 132, and lower head supports 130 and mandible support arms 114. Once the proper position of the mandible support is achieved on the side component 112, the turn-tab adjustment mechanism 122 can be rotated to tighten the mandible support arm 114 onto the side component 112.

An example of the turn-tab adjustment mechanism 122 is shown in FIG. 5 and includes a backing panel 124 with a mounting or threaded stud 144 on one side, and a threaded aperture 160, on an opposite side. An attaching head 180 is mounted onto the backing panel 124. The attaching head 180 includes a centrally-located flush-mounted aperture and a hingedly connected flip-up turn-tab 12. A set screw 142 has a length such that it can be screwed into the centrally located aperture 136 and connected to the flush mounted hole in the backing panel 124, thereby joining the attaching head 180 to the backing panel 124. A flip-up turn-tab 140 can be pivoted upward or raised 90-degrees or any suitable angle, in order to effect rotation of the turn-tab adjustment mechanism 122 in the clockwise and counterclockwise directions. The flip-up turn-tab can be any suitable shape including semi-circular as shown.

In operation, the threaded stud 144 of the backing panel 124 shown in FIG. 5 can be inserted into the threaded boss 120 in the first component that is being attached to the second component. The threaded boss of the first component can be nylon or brass. The attaching head 180 is mounted onto the backing panel 124, and the set screw 142 is guided through the aperture 136 of the attaching head 180 to the threaded aperture 160 in the backing panel 124 where it is rotatably secured. The flip up turn-tab 140 can be raised and rotated to thereby turn the entire turn-tab adjustment mechanism 122 to tighten the first component onto the second component.

Another example of the turn-tab adjustment mechanism 222 as shown in FIG. 6, includes a backing panel 224 with a threaded stud 244 and a hollow spline stud 260. The attaching head 280 in this example has a spline portion 246 and a hinged flip-up turn-tab 240. The flip-up turn-tab 240 is hingedly mounted to the attaching head as shown in FIG. 6, and can be pivoted upward or raised 90-degrees or any suitable angle, in order to effect rotation of the turn-tab adjustment mechanism in the clockwise and counterclockwise directions. In operation, the threaded stud 244 of the backing panel 224 is inserted into one of the threaded bosses 220 in the second component. The spline portion 246 of the attaching head 280 is fittedly inserted into the hollow spline stud 260 of the backing panel to mount the attaching head 280 thereto. The flip up turn-tab 240 can then be raised and rotated to thereby turn the entire turn-tab adjustment mechanism 222 to tighten the first component onto the second component.

Figure 7A:
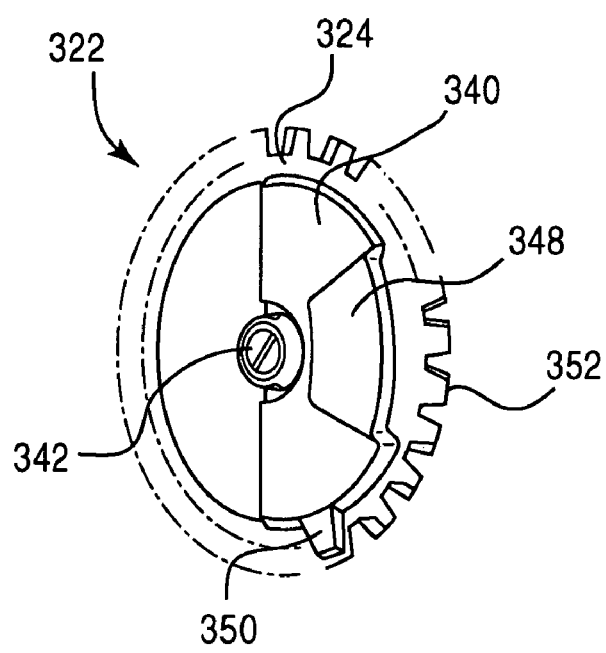
FIGS. 7a and 7b illustrate exemplary attachment devices according to the present invention.
Figure 7B:
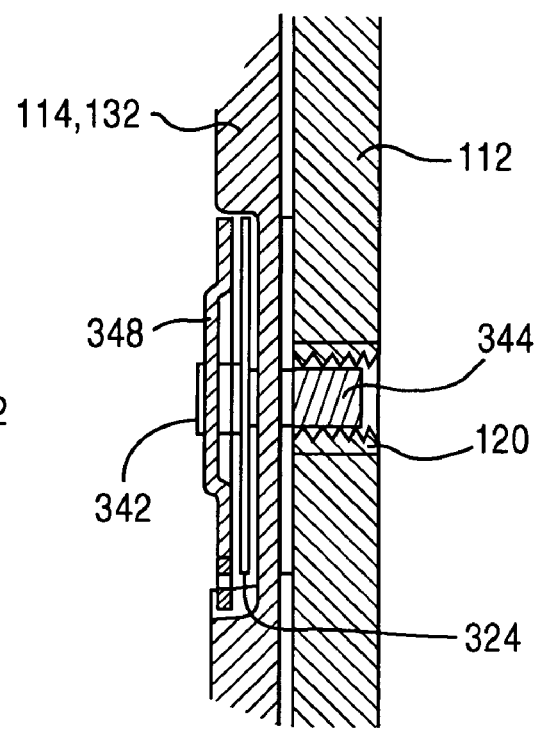

A further example of the turn-tab adjustment mechanism 322, shown in FIGS. 7a and 7b, includes a backing panel 324 with a threaded stud 344 and a threaded hole through which a set screw 342 is mounted. The backing panel 324 includes a plurality of notches 352 around an inner perimeter thereof. An attaching head 380 includes an aperture for receiving the set screw 342, and a hinged flip-up turn-tab 340. The flip-up turn-tab 340 in this example includes a key 350 extending from an outer perimeter thereof. The key 350 is designed to be seated one of the corresponding notches 352 on the backing panel 324 to prevent rotation of the attaching head 380 with respect to the backing panel. The flip-up turn-tab 340 also includes a thumb tab 348 for ease of gripping the tab 340.

In operation, the threaded stud 344 of the backing panel 324 is inserted into a threaded boss 320 of the first component, such as the mandible support or occipital/deltoid support 132, and a threaded boss of the second component, such as the side component 112 shown in FIG. 7b. The threaded bosses 120 can be nylon or brass. The attaching head 380 is mounted onto the backing panel 324, and the set screw 342 is flush mounted in the aperture of the attaching head 380. In order to adjust the turn-tab adjustment mechanism 322, the turn-tab 340 can be pivoted upward in order to effect rotation of the turn-tab adjustment 322 mechanism in the clockwise and counterclockwise directions to tighten or loosen the connection between the components. The turn-tab 322 can be pivoted or folded downward so that the key 350 is seated into any one of the plurality of notches 352 on the backing panel 324.

The turn-tab adjustment mechanism 122 requires no tools and has no loose parts. As such, the turn-tab adjustment mechanism 122 allows for fast easy adjustment and attachment of various components of the cervical support system. Materials that can be used to form the turn-tab adjustment mechanism include metals or high tolerance molded plastic.

Example embodiments of the present invention have now been described in accordance with the above advantages. It will be appreciated that these examples are merely illustrative of the invention. Many variations and modifications will be apparent to those skilled in the art.

We claim:

1. An apparatus for restricting head and neck movement, comprising:

a pair of arcuate side members, each having a front portion, a rear portion, an outer portion and in inner portion;

a primary supporting member bridging the rear portions of the pair of arcuate side members;

a secondary supporting member mounted on each of the outer portions of the pair of arcuate side members and arranged to extend in a direction opposite from the primary supporting member; and a plurality of adjustment devices for securing the primary and secondary supporting members to the pair of arcuate side members;

wherein the secondary supporting member comprises a mandible support with a pivotal chin channel.

2. The apparatus according to claim 1, wherein the secondary supporting member comprises a mandible support having a distal end and a proximal end, the mandible support being mounted by the proximal end to each side member.

3. The apparatus according to claim 2 wherein the secondary supporting member further comprises a lower head support pivotally mounted to the distal end of the mandible support.

4. The apparatus according to claim 2, wherein the mandible support is laterally and longitudinally adjustable on the outer poition of the pair of arcuate side members.

5. The apparatus according to claim 2, wherein the primary supporting member comprises an occipitalldeltoid supporting member.

6. The apparatus according to claim 1, wherein the plurality of adjustment devices comprise a plurality of turn-tab adjustment mechanisms.

7. The apparatus according to claim 6, wherein each turn-tab adjustment mechanism comprises a flip up portion, an attaching head hingedly connected to the flip up portion; a backing panel; a set screw for mounting the attaching head to the backing panel; and a mounting stud for mounting the backing panel into at least one of the primary supporting member and the secondary supporting member.

8. The apparatus according to claim 7, wherein each turn-tab adjustment mechanism is screwed into the apparatus through threaded bosses embedded therein.

9. The apparatus according to claim 1, wherein the arcuate member has a plurality of apertures for ventilating the arcuate member.

10. The apparatus according to claim 1, wherein the arcuate member forms a crescent shape.

11. The apparatus according to claim 1, wherein the secondary supporting member on each of the outer portions of the pair of arcuate side members is independent of the other.

12. An apparatus for restricting head and neck movement to a body comprising:

A pair of side members arranged parallel to each other;

primary supporting means for supporting an occipital/deltoid region of the body and bridging the pair of side members;

secondary supporting means for supporting a jaw portion of the head fastened to each of the pair of side members; and fastening means for fastening the primary supporting means and secondary means to the pair of side members, wherein the secondary supporting means fastened to each of the pair of side members is independent of the other.

13. The apparatus according to claim 12, wherein the fastening means comprise turn-tab adjustment mechanisms.

14. The apparatus according to claim 12, wherein the secondary supporting means comprises a mandible support.

15. The apparatus according to claim 12, further comprising cushioning means for cushioning an inner surface of at least one of the primary supporting means, the pair of side members, and the secondary supporting means.

16. The apparatus according to claim 12, wherein the primary supporting means comprises an occipital/deltoid support.

17. The apparatus according to claim 12, wherein the secondary supporting means comprises a lower head support.

* * * * *